(12) United States Patent
Mezghani et al.

(10) Patent No.: US 9,532,732 B2
(45) Date of Patent: Jan. 3, 2017

(54) METHOD AND SYSTEM FOR KNEE JOINT EVALUATION AND DIAGNOSTIC AID IN NORMAL AND PATHOLOGIC STATE

(75) Inventors: Neila Mezghani, Montréal (CA);
Jacques De Guise, Montréal (CA);
Guy Grimard, Ville Mont-Royal (CA);
David Baillargeon, Blainville (CA);
Youssef Ouakrim, Montréal (CA);
Gérald Parent, Mascouche (CA);
Alexandre Fuentes, Montréal (CA);
Patrick Lavigne, Blainville (CA);
Pierre Ranger, Ste-Dorothée (CA)

(73) Assignee: Emovi Inc., Laval (CA)

( * ) Notice: Subject to any disclaimer, the term of this patent is extended or adjusted under 35 U.S.C. 154(b) by 423 days.

(21) Appl. No.: 12/772,701

(22) Filed: May 3, 2010

(65) Prior Publication Data

US 2011/0270132 A1 Nov. 3, 2011

(51) Int. Cl.
*A61B 5/103* (2006.01)
*A61B 5/00* (2006.01)

(52) U.S. Cl.
CPC .......... *A61B 5/1038* (2013.01); *A61B 5/4528* (2013.01); *A61B 5/6828* (2013.01); *A61B 5/7264* (2013.01);
(Continued)

(58) Field of Classification Search
CPC ... A61B 5/1038; A61B 5/4528; A61B 5/4585; A61B 5/7264
(Continued)

(56) References Cited

U.S. PATENT DOCUMENTS 4,306,571 A * 12/1981 McLeod, Jr. ................ 600/595
5,533,519 A * 7/1996 Radke et al. ................ 600/595
(Continued)

FOREIGN PATENT DOCUMENTS

AU 2007209792 9/2007
CA 2287771 5/2001
(Continued)

OTHER PUBLICATIONS

Jones et al., Knee Function Classification an overview of the Dempster-Shafer based classifier, 2006, Ninth Symposium on 3D Analysis of Human Movement, 4 pages.*
(Continued)

*Primary Examiner* — Adam J Eiseman
(74) *Attorney, Agent, or Firm* — Benoît & Côté Inc.

(57) ABSTRACT

The present document describes an apparatus and method for identifying and characterizing a problem of a knee joint. In accordance with an embodiment, the method comprises receiving biomechanical data from sensors and generating a biomechanical profile based on the biomechanical data, the biomechanical data being representative of a movement of the knee joint. The method also involves, in a processing device, classifying the biomechanical profile of the knee joint in one of multiple classes of knee joint problems by applying a pattern recognition technique to a normative biomechanical profile associated to the one of the multiple classes, each one of the multiple classes corresponding to at least one knee joint problem; based on the classifying, identifying the problem as comprising the at least one knee joint problem of the one of the multiple classes; and archiving the problem identified in a storing device to make the problem accessible during consultation.

19 Claims, 5 Drawing Sheets

(52) U.S. Cl.
CPC ........ *A61B 5/7267* (2013.01); *A61B 2560/045* (2013.01)

(58) Field of Classification Search
USPC .............................................. 600/587, 595
See application file for complete search history.

(56) References Cited

U.S. PATENT DOCUMENTS

| | | | |
|---|---|---|---|
| 6,777,241 | B1 | 8/2004 | Naumann |
| 7,011,605 | B2 | 3/2006 | Shields |
| 7,184,814 | B2* | 2/2007 | Lang ...................... A61B 5/055 324/307 |
| 7,239,908 | B1* | 7/2007 | Alexander ............. A61B 5/055 378/21 |
| 7,481,780 | B2 | 1/2009 | de Guise et al. |
| 7,881,768 | B2* | 2/2011 | Lang ...................... A61B 5/055 600/407 |
| 7,988,647 | B2* | 8/2011 | Bunn et al. ................... 600/595 |
| 2002/0087274 | A1* | 7/2002 | Alexander ............ A61B 5/1114 702/19 |
| 2003/0212480 | A1 | 11/2003 | Lutter |
| 2007/0015995 | A1* | 1/2007 | Lang ...................... A61B 5/055 600/407 |
| 2011/0054486 | A1 | 3/2011 | Linder-Ganz |

FOREIGN PATENT DOCUMENTS

| | | |
|---|---|---|
| JP | 2004261525 A | 9/2004 |
| WO | WO 01/32080 | 5/2001 |
| WO | WO 2009/067782 | 6/2009 |
| WO | WO 2009/090200 | 7/2009 |

OTHER PUBLICATIONS

Limbourg, et al., Reliability assessment and optimization under uncertainty in the Dempster-Shafer framework, 2004, 27th ESReDA seminar, Glasgow, GB, pp. 77-89.*

Begg, R. and J. Kamruzzaman, A machine learning approach for automated recognition of movement patterns using basic, kinetic and kinematic gait data. J Biomech, 2005. 38(3): p. 401-8.

Beynon, M.J., L. Jones, and C.A. Holt, Classification of osteoarthritic and normal knee function using three-dimensional motion analysis and the Dempster-Shafer theory of evidence. IEEE transaction on systems, man, and cybernetics, 2006. 36(1): p. 173-186.

Fuentes, A., et al. Automatic Classification of 3D Kinetic Data of Healthy and ACL Deficient Participants in 64e Réunion annuelle de l'Association Canadienne d'Orthopédie. 2009. Whistler, Colombie-Britannique, Canada, 2 pages.

Gazzoni, M., D. Farina, and R. Merletti, A new method for the extraction and classification of single motor unit action potentials from surface EMG signals. J Neurosci Methods, 2004. 136(2): p. 165-77.

Jones, L., et al., An application of the Dempster-Shafer theory of evidence to the classification of knee function and detection of improvement due to total knee replacement surgery. J Biomech, 2006. 39(13): p. 2512-20.

Lafuente, R., et al., Design and test of neural networks and statistical classifiers in computer-aided movement analysis: a case study on gait analysis. Clin Biomech (Bristol, Avon), 1998. 13(3): p. 216-229.

Lai, D.T., et al., Automatic recognition of gait patterns exhibiting patellofemoral pain syndrome using a support vector machine approach. IEEE Trans Inf Technol Biomed, 2009. 13(5): p. 810-7.

Mezghani, N., A. Mitiche, and M. Cheriet, Bayes classification of online arabic characters by Gibbs modeling of class conditional densities. IEEE Trans Pattern Anal Mach Intell, 2008. 30(7): p. 1121-31.

Mezghani, N., et al., Automatic classification of asymptomatic and osteoarthritis knee gait patterns using kinematic data features and the nearest neighbor classifier. IEEE Trans Biomed Eng, 2008. 55(3): p. 1230-2.

Mezghani, N., et al., Hierarchical analysis and classification of asymptomatic and knee osteoarthritis gait patterns using a wavelet representation of kinetic data and the nearest neighbor classifier. Journal of Mechanics in Medicine and Biology, 2008. 8(1): p. 45-54.

Sekine, M., et al., Discrimination of walking patterns using wavelet-based fractal analysis. IEEE Trans Neural Syst Rehabil Eng, 2002. 10(3): p. 188-96.

T. Chau. A review of analytical techniques for gait data. Part 1: fuzzy, statistical and fractal methods. Gait and Posture, 13(1):49-66, Feb. 2001.

T. Chau. A review of analytical techniques for gait data. Part 2: Neural network and wavelet methods. Gait and Posture, 13(2):102-120, Avril 2001.

W. L. Wu and F. C. Su. Potential of the back propagation neural network in the assessment of gait patterns in ankle arthrodesis. Clinical Biomechanics, 15(2):143-145, Feb. 2000.

Wolf, A. and A. Degani, Recognizing knee pathologies by classifying instantaneous screws of the six degrees-of-freedom knee motion. Med Biol Eng Comput, 2007.45(5): p. 475-82.

PCT—International Search Report (ISR)—PCT/CA2011/000514 (Form PCT/ISA/210)—Aug. 17, 2011—3 pages.

* cited by examiner

METHOD AND SYSTEM FOR KNEE JOINT EVALUATION AND DIAGNOSTIC AID IN NORMAL AND PATHOLOGIC STATE

CROSS-REFERENCE TO RELATED APPLICATIONS

This application is the first disclosure of this subject matter.

TECHNICAL FIELD

This description relates to the field of knee joint movement analysis methods and apparatuses. More particularly, this description relates to apparatuses and methods for evaluating knee joint pathologies and injuries based on kinematic data.

BACKGROUND

Studies have shown that musculoskeletal disorders represent the second most important health-related costs in almost all industrialized countries, close behind cardiovascular diseases, and ahead of cancer and neurological diseases. By musculoskeletal disorders, it is intended to refer to disease of cartilage, bone, muscle, ligaments and tendons. With the current progressive increase in life expectancy, musculoskeletal problems have become more prevalent in the population, resulting in an increase in the number of available pharmacological treatments and therapeutic devices. With the emergence of new treatment modalities came the development new instruments for the detection, evaluation and monitoring of knee joint injuries and pathologies.

The knee is an extremely complex joint necessitating a perfectly coupled three-dimensional range of movement for proper function. Knee joint functions are thus better evaluated via analysis of their three-dimensional components, using a quantified functional approach reflective of movements of bones of the knee joint in one of the three-dimensional planes.

Current methods involve the use of radiological examinations (such as X-rays, MRI, CT-Scans). Such exams however typically remain limited in terms of their capacity to evaluate various functional aspects of the knee joint, and typically cannot be performed while the knee joint is moving (i.e. they are static in nature).

Other existing methods used to evaluate knee joints function typically involve static imaging combined with manual testing (ligament laxity). Since these tests rely on manual testing and patient compliance, they are tainted by a certain amount of subjectivity.

Some existing methods permit the quantification of anteroposterior movement of the tibia with respect to the femur (such as the KT-1000). These methods however do not permit precise and reliable evaluation of the knee joint as they are typically limited to performing a static evaluation of a translation movement. Such methods are typically not suitable for performing an evolution as a movement is being performed by the knee joint.

There is therefore a need for an improved apparatus and method for evaluating knee joint function and disorders or pathologies, which addresses shortcomings associated with the prior art, or at least provides a useful alternative.

SUMMARY

According to an embodiment, there is provided a method for identifying and characterizing a problem of a knee joint.

In accordance with an embodiment, the method comprises receiving biomechanical data from sensors and generating a biomechanical profile based on the biomechanical data, the biomechanical data being representative of a movement of the knee joint. The method also involves, in a processing device, classifying the biomechanical profile of the knee joint in one of multiple classes of knee joint problems by applying a pattern recognition technique to a normative biomechanical profile associated to the one of the multiple classes, each one of the multiple classes corresponding to at least one knee joint problem; based on the classifying, identifying the problem as comprising the at least one knee joint problem of the one of the multiple classes; and archiving the problem identified in a storing device to make the problem accessible during consultation.

According to another embodiment, there is provided an apparatus for identifying and characterizing a problem of a knee joint. The apparatus comprises: sensors for attachment to a knee joint, the sensors for gathering biomechanical data representative of a movement of a knee joint; a processor in communication with the sensors; and a memory device accessible by the processor. The memory device stores instructions for retrieval by the processor to implement the processor to: receive the biomechanical data from the sensors; generate a biomechanical profile based on the biomechanical data; classify the biomechanical profile of the knee joint in one of multiple classes of knee joint problems by applying a pattern recognition technique to a set of normative biomechanical profiles associated to the multiple classes, each one of the multiple classes corresponding to at least one knee joint problem; based on the classifying, identify the problem as comprising the at least one knee joint problem of the one of the multiple classes; and archive the problem identified to allow retrieval of the problem during a medical consultation.

According to another embodiment, there is provided a computer readable media storing instructions for implementing a processor to identify a problem of a knee joint. The instructions comprise coding for implementing the processor to: receive biomechanical data from sensors, the biomechanical data being representative of a movement of the knee joint; generate a biomechanical profile based on the biomechanical data; classify the biomechanical profile of the knee joint in one of multiple classes of knee joint problems by applying a pattern recognition technique to a set of normative biomechanical profiles associated to the multiple classes, each one of the multiple classes corresponding to at least one knee joint problem; based on the classifying, identify the problem as comprising the at least one knee joint problem of the one of the multiple classes; and archive the problem identified in a storing device to make the problem accessible during consultation.

In the present description, the term "kinematic data" refers to data reflective of a combination of position, speed and acceleration of a body member such as a bone involved in a knee joint for example, irrespective of any physical force applied thereto. Kinematic data is obtainable using motion sensors such as those employed in creating animation-type movies.

By comparison, the term "kinetic" refers to the forces applied to the knee joint, while ground reaction forces refer to forces applied to a limb, from a given surface such as the ground during a gait cycle for example. Both ground reaction forces and kinetic data are obtainable using force sensors placed at various areas such as on the limb and the ground.

In addition, the term "normative" is used in the present description as meaning representative. A "normative biomechanical profile" is thus intended to refer to a biomechanical profile which is known to be representative or which is associated to a specifically known knee joint problem or class of knee joint problem(s). Such a normative profile can be compiled from profiles of a number of subjects having a diagnosed problem for example, and the data optionally normalized or averaged for all these subjects.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

There will now be described in reference to the appended drawings, an evaluation and diagnosis apparatus and method for evaluating a knee joint to detect knee joint pathologies and/or injuries. The described apparatus and method are adapted to quantify: (i) a function of a knee joint movement, (ii) an impact of a pathology and/or an injury on biomechanics of the knee joint; (iii) an impact of a given treatment on the knee joint biomechanical function.

In addition, the presently described apparatus and method does not require such advance input on a probable problem to be found, which is contrary to currently available evaluation apparatuses and methods. These are typically limited in that they do require advance input as to probable classes into which a given problem for a knee joint to be evaluated will fall, in order to perform a multi-classification (i.e. identify that the problem falls within one or more of such multiple classes).

Figure 1A:
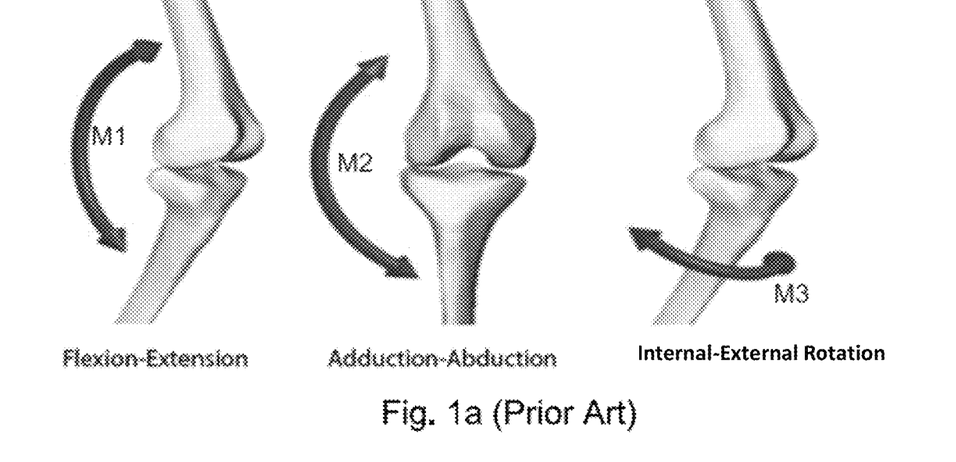
FIG. 1a is an illustration of the femur and the tibia of a knee joint, which shows three planes of motion of the knee joint, in accordance with common general knowledge associated with prior art.
Figure 1B:
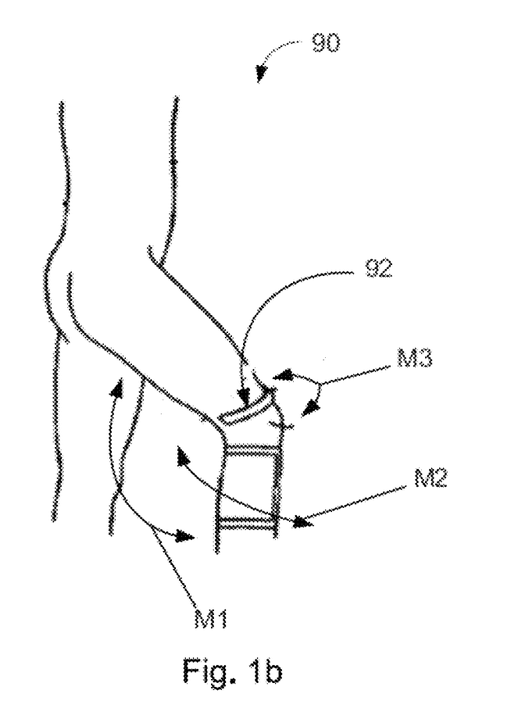
FIG. 1b is an illustration of a patient's knee joint with a sensor, and showing the three planes of motion of FIG. 1a, in accordance with an embodiment.

Referring now to the drawings, and more particularly to FIG. 1b, there is shown a typical patient 90, here a human, whereby knee joint kinematic data is collected using a three-dimensional kinematic data sensor device 92 which is worn by the patient 90 over a knee joint. The sensor device 92 is non-invasive and remains on a surface of the skin of the patient 90. Many types of sensor devices can be used for such purposes. Examples include optical tracking devices; electromagnetic tracking devices and accelerometers.

As seen in FIGS. 1a and 1b, a knee joint is able to move according to three different planes of motion; each of these allowing two degrees of freedom.

First plane of motion—Flexion-Extension illustrated by arrow M1: This motion refers to the capacity of movement of the knee joint to move the leg towards (flexion) the back of the thigh, and away (extension).

Second plane of motion—Abduction-Adduction illustrated by arrow M2: This motion refers to the capacity of movement of the knee joint to arc the leg towards a center axis of the body. As an example, an Abduction-Adduction plane can be apparent in a subject who has a "cowboy-like" demeanour, although this type of movement is typically subtle in most human patients.

Third plane of motion—Internal-External Rotation illustrated by arrow M3: This motion refers to the capacity of movement of the knee joint to rotate about itself (or about an axis of rotation substantially along a longitudinal plane of the leg).

The sensor device monitors kinematic data reflective of each of the three above described plane of motion. The kinematic data gathered is thus indicative of three planes of movement (6 degrees of freedom) per knee joint of a patient.

As most knee joint disorders (be it knee osteoarthritis, anterior cruciate ligament rupture, meniscal tear, patellofemoral syndrome) have a concrete impact on knee joint movement, these can be associated to specific kinematic data gathered during knee movement. Inversely, an abnormal knee joint movement is determined by kinematic data recordings and in some instances is also informative of a patient's predisposition towards developing a given knee joint injury and/or pathology.

A database stores normative biomechanical profiles each associated with a given knee joint pathology and/or injury. Each of these normative profiles is pre-loaded based on kinematic data gathered from various patients. For a given normative profile, various diagnoses made using a set of various means, such as imagery and expert evaluation, are correlated with one another in order to ensure that the final diagnosis associated to the normative profile is accurate. In this way, the normative profiles are each associated to a type of injury and/or pathology.

Upon comparison of the normative profiles to a biomechanical profile of a knee joint of a patient, at least a knee joint problem classification is achieved directly and automatically without use of imagery, and according to a quantified level of reliability, as described in greater detail below.

Figure 2:
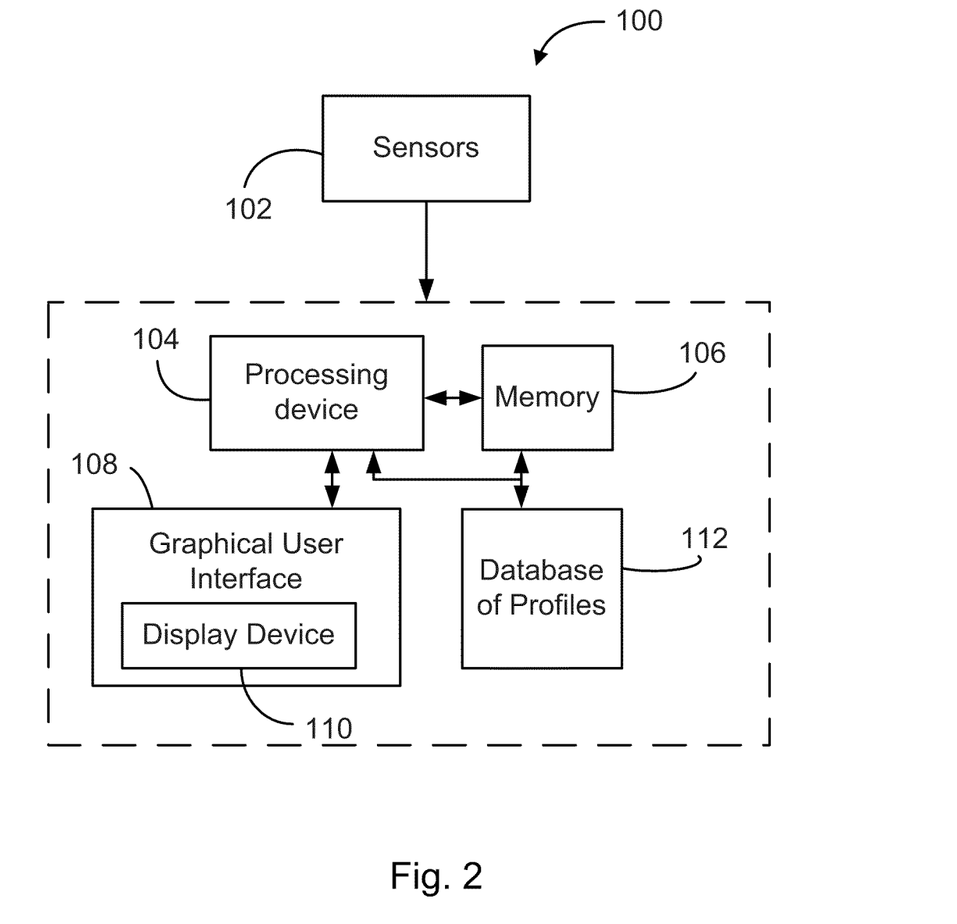
FIG. 2 is a schematic illustration of an apparatus for identifying and characterizing a knee joint problem, in accordance with another embodiment.

FIG. 2 is a schematic illustration of an apparatus for identifying and characterizing a knee joint problem, in accordance with another embodiment. The apparatus 100 has a set of sensors 102 in communication with a processing device 104, a memory 106, a graphical user interface (GUI) 108, a display device 110, and a database 112.

In one embodiment, the sensors 102 have tracking devices (not shown) to track position, speed and acceleration of various parts of the knee joint during a movement of the knee joint to generate kinematic data associated to the knee joint movement as it is being performed. In this case, the sensors 102 are sensing devices adapted to be attached to a patient's knee joint or other portion of the limb under evaluation. In other cases, the sensors 102 are force sensors positioned so as to measure either one or a combination of kinetic data and ground reaction forces during movement, as later described. Other examples of sensors 102 include, but are not limited to, cameras, accelerometers and gyroscopes which are respectively positioned, for example, on the femur and the tibia of the patient. In any given case, the sensors 102 generate biomechanical data associated to the movement and as it is performed.

Knee joint movements include for example, gait, squats, lunges or a combination of these movements. The biomechanical data is representative of the knee joint movement in according to at least one dimension of movement. Once biomechanical data is gathered, or as it is gathered, it is sent from the sensors 102 to the processing device 104, and optionally stored in the memory 106.

Once received at the processing device 104, either after the movement has passed or during the time the movement is being performed, the biomechanical data is processed in the processing device 104, in accordance with instructions stored in the memory 106. Such processing results in a biomechanical profile of the knee joint. The biomechanical profile is generated based on the biomechanical data and is indicative of at least one of the three planes of motion M1, M2 and M3 of the knee joint, as described above in relation to FIGS. 1a and 1b.

Normative profiles are stored in the database 112 in association with at least one class of knee joint problem(s). A class has one or more knee joint problems which are known to be associated to quantifiable effects on the biomechanics of knee joints; and thence on the biomechanical profiles of knee joints.

If the class defines a single knee joint problem, then the class defines a particular known knee joint injury, pathology or biomechanical deficit of knee joints. If the class regroups various known knee joint problems, then it is associated to a combination of injuries, pathologies and biomechanical deficits, which are for example, generally documented in the medical field as falling under a given particular category of knee joint problems. In one embodiment, the normative profile(s) associated to each class are biomechanical profile(s) which are accepted in the medical field as being indicative of a particular knee joint problem, or a plurality of particular knee joint problems.

Still referring to FIG. 2, the normative profiles are retrieved from the database 112 by the processing device 104. The processing device 104 then proceeds by applying a pattern recognition technique on these normative profiles and the biomechanical profile, from which a classification of the biomechanical profile of the knee joint under analysis is made by the processing device 104.

The pattern recognition and classification is performed in the processing device 104. Various types of pattern recognition (also referred to pattern classification) techniques can be used, as per instructions (also referred to as coding) stored in the memory 106. For example, any computer implemented pattern recognition between the biomechanical profile and the normative profiles is used such as, for example, any type of machine learning technique to provide an automated machine classification and decision-making based on the biomechanical profile. A non-exhaustive list of possible implementations includes: a parametric or a non parametric technique, a neural network, a nearest neighbour classification technique, a projection technique, a decision tree technique, a stochastic method, genetic algorithms and an unsupervised learning and clustering technique.

The processing device 104 proceeds to classify the biomechanical profile of the knee joint into one of several classes of known knee joint problems, based on results from the pattern recognition technique.

Once the classification of the biomechanical profile is done, a problem is identified based on the class(es) in which the biomechanical profile has been classified, and the identified problem is outputted by the processing device 104. More particularly, the problem identified corresponds to the knee joint problem in the class of knee joint problems under which the biomechanical profile has been classified by the processing device 104. For example, if the biomechanical profile is classified in a class of normative profiles associated to a meniscus tear, then the identified problem corresponds or at least comprises the meniscus tear. In one instance, the problem identified can in fact combine more than one knee joint problem when the biomechanical profile is classified in a class associated to more than one problem.

In addition to the normative profiles, the database 112 can store the biomechanical profile for the knee joint, any type of patient-identification data, and the biomechanical data received from the sensors 102. In one embodiment, the database 112 stores a plurality of sets of normative profiles; each set being associated to a particular class of pathology(ies) and/or injury(ies) and/or biomechanical deficit(s).

The GUI 108 and the display device 110 are in communication with one another and with the processing device 104 (and in one embodiment, with the memory 106). The GUI 108 receives either one or a combination of the classification for the knee joint under analysis and the identified problem, whichever appropriate in a specific case. In either case, however, the GUI 108 displays either one or a combination of the classification and the particular problem identified, including a description of the knee joint problem(s) involved,) on the display device 110. The GUI may also display the biomechanical profile generated from the biomechanical data.

The GUI allows user interaction such that a particular display setting is activated on the display device 110, to show either or a combination of: the biomechanical profile, the diagnosis and the normative profile(s) relevant to the problem identified, in accordance with a user preferences.

Still in reference to FIG. 2, it is noted that in one embodiment, the sensors 102 are embodied as a commonly available three-dimensional (3D) knee movement analyser such as the one described in U.S. Pat. No. 7,291,119, and having a set of tracking sensors suited to obtain kinematic data for tibio-femoral movements of a knee joint. The sensors 102 can however be of any type of dynamic 1D, 2D or 3D knee analyzer based on either one or a combination of available technologies such as optical, electromagnetic, accelerometers, which provide for the monitoring of an acceleration, position and speed.

In addition to the above-described apparatus, it is noted that in one embodiment, the apparatus 100 is adapted to perform any of the below-detailed steps of a method 300 described in relation to FIG. 3. For example, one embodiment of the apparatus 100 is adapted to output a quantified function of the knee joint during the movement (i.e. with respect to time). In the same manner, the apparatus 100 can also be adapted to compare a current biomechanical profile with an older (also referred to as past or previous) biomechanical profile for the same knee joint, and quantify a progression (improvement or degradation) of the problem in the given period between the current and the past biomechanical profiles for example. Other optional functionalities also include sorting a plurality of identified knee joint problems such as pathologies, injuries and biomechanical deficits in terms of their respective degree of importance, priority or combination thereof; normalize the biomechanical data prior to generating and displaying the biomechanical profile; and generating a complete report for a patient's knee joint(s) under analysis.

It is noted that while the apparatus 100 is described as receiving biomechanical data from the sensors 102, such biomechanical data represents, in one embodiment, only kinematic data. In other implementations, however, the biomechanical data is any one of, or a combination of: kinematic data, kinetic data and ground reaction forces. In one embodiment, additional data such as patient data, professional diagnostic data, and clinical information is received as well. It is noted that the apparatus 100 is able to rely only on the kinematic data in order to provide for the herein described functionalities (i.e. in one embodiment, the kinematic data is a sole input to the processing device 104).

Figure 3:
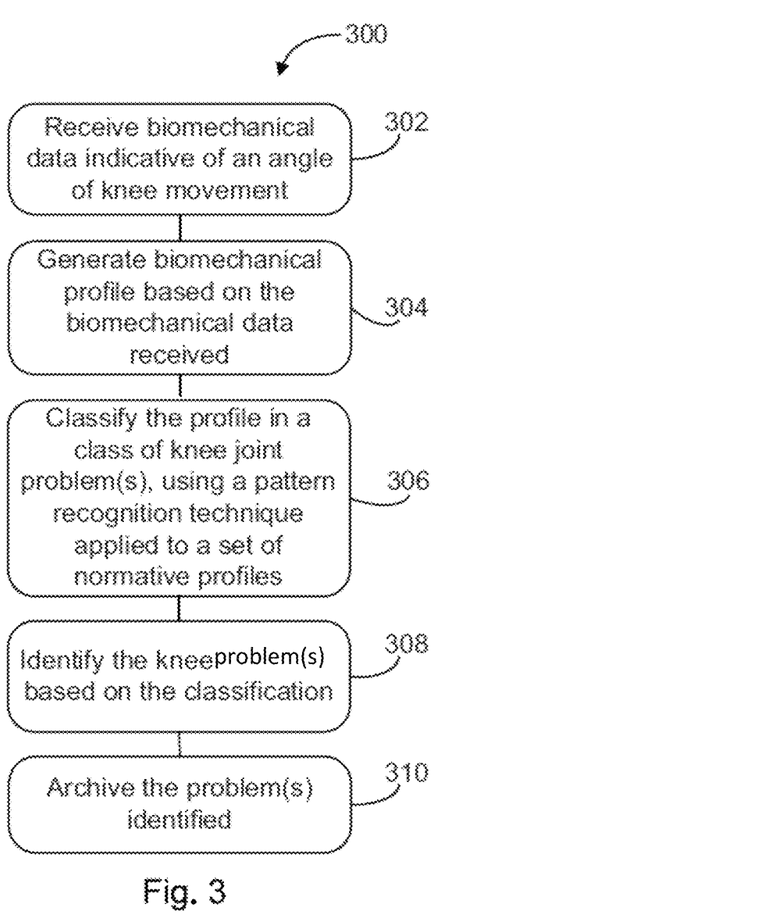
FIG. 3 is a flow chart of a method for identifying and characterizing a knee joint problem, in accordance with an embodiment.

FIG. 3 shows a flow chart of a method 300 for evaluating a knee joint and identifying a knee joint problem, in accordance with an embodiment.

In step 302, biomechanical data is received from a sensor. The biomechanical data is representative of a movement performed by a knee joint, in accordance with one of the three planes of movement defined above in reference to FIG. 1a-1b. In one embodiment, the biomechanical data is received while the movement is being performed by the knee joint.

In step 304, a biomechanical profile is generated based on the biomechanical data received. The biomechanical profile is indicative of at least one of the three planes of motion of the knee joint as the movement is performed.

In step 306, the biomechanical profile is classified in at least one class of knee joint problem(s) using a pattern recognition technique applied to at least one set of normative profiles. The set of normative biomechanical profiles are pre-associated to one of multiple classes of knee joint problems (i.e. when there is more than one set, each set is associated to a single class).

In one embodiment, step 306 involves comparing the biomechanical profile to the set of normative biomechanical profiles. In one embodiment, a correlation model is used.

As described also hereinabove, a class of knee joint problem(s) defines one or more known knee joint problem known to have an effect on the biomechanics of the knee joint (i.e. the biomechanical profile will be reflective of one or more of the knee joint problems). If the class is associated to a single knee joint problem, then the class defines a particular known knee joint injury, pathology or biomechanical deficit associated to knee joints. If the class regroups various known knee joint problems, then the class is associated to a combination of either one of injuries, pathologies and biomechanical deficits for example. Such problems are generally documented in the medical field as falling under a given particular type of knee joint problem. In some instances, one biomechanical profile is classified in multiple classes, in which case the knee joint has deficiencies encompassing multiple types of knee joint problems.

In step 308, the knee joint problem(s) proper to the particular knee joint under analysis is(are) identified based on the results of step 306. Since each one of the multiple classes is indicative of at least one particular knee joint problem (i.e. pathology, injury or biomechanical deficit), the at least one class according to which the biomechanical profile is classified is indicative of a particular knee joint problem for the knee joint. The identification of such knee joint problem corresponds is performed by a computer device in accordance to this method 300 and thereby provides an assistance in medical diagnosis.

In step 310, the identified problem(s) is(are) archived for further analysis, reporting or display on an output of any type, such as email or other network-based notification addressed to authenticated users for example.

In one embodiment where step 306 involves classifying the biomechanical profile into one of the multiple classes being associated to multiple knee joint problems, the problem identified in step 308 comprises more than one problem. In such a case, the method 300 involves another optional step (not illustrated in FIG. 3) of sorting the multiple identified problems according to a set of priority levels pre-defined for a list of possible knee joint problems. Alternatively or additionally, the sorting is done according to a respective degree of severity associated with each one of the diagnosed knee joint problems.

In one embodiment, the set of priority levels are established by a user entering the levels manually via user interaction with a graphical user interface (GUI). In another embodiment, the levels are set by default in a processing device implementing the method 300.

In order to evaluate the degree of severity of a diagnosed knee joint problem, it is first noted that the one or more normative biomechanical profiles associated with the diagnosed knee joint problem provide, in one embodiment, a data range within which the patient's biomechanical profile is determined to fit via the pattern recognition in step 306. The shape of the patient's biomechanical profile fitting within this range is analyzed in order to provide for the degree of severity. In a specific case where the patient's biomechanical profile has a shape defined within an extremity of the data range in the normative profile, for example, the degree of severity is said to be higher than if the shape were defined within a mid section of the data range. Other techniques for determining the degree of severity can also be used based on any kind of error analysis technique.

In one embodiment, step 304 also involves quantifying a function of the knee joint with respect to a time elapsed during the movement.

In one embodiment, the pattern recognition technique applied in step 306 is any type of computer implemented pattern recognition which includes for example machine learning techniques enabling automated machine classification and decision-making based on the biomechanical profile and normative profiles The classifying in step 306, involves in one embodiment, determining an amount of similarity (also referred to as adherence). The amount of similarity is relied upon for the identification step 308. As the amount of similarity is also indicative of a degree of reliability in the classifying performed in step 308, it also serves as a reliability indication.

Still in reference to FIG. 3, it is noted that in addition to step 310 as illustrated, the method 300 involves in one example the displaying of a graphical user interface (GUI) which allows user interaction. For example, the user is able to enter preferences, or request a particular type of display of particular data.

Figure 4A:
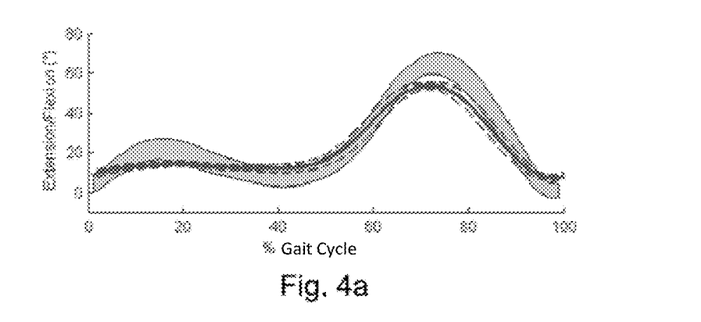
FIG. 4a is a graphical illustration of a degree of extension-flexion of a knee joint during a gait cycle, in accordance with an embodiment.
Figure 4B:
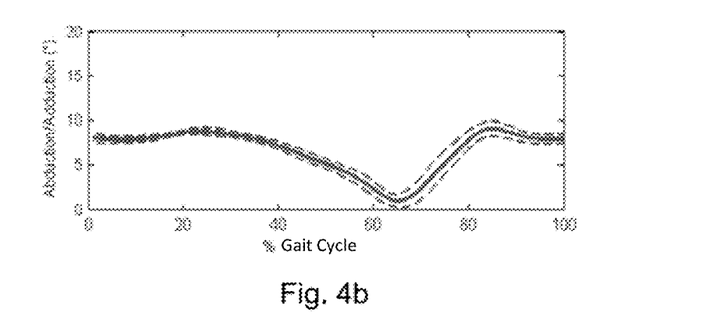
FIG. 4b is a graphical illustration of a degree of abduction-adduction of a knee joint during a gait cycle, in accordance with an embodiment.

In addition, the method 300 also optionally involves displaying the biomechanical profile in accordance with a given format. The format can be as per a user entered preference(s) or set by default. In one embodiment, the displaying optionally involves generating a set of graphical illustrations to represent the data according to at least one of the three planes of motion as they are sensed by the motion sensor during the movement. In one embodiment, the planes of motion are provided in terms of degrees, and the time elapsed during the movement of the knee joint is provided in terms of percentage of the movement performed. Examples of graphical illustrations are provided by FIGS. 4a, 4b and 4c, which respectively illustrate a graph of plane degrees versus percentage of elapsed movement (here a gait cycle); for each one of the three plane of motion M1, M2 and M3 as described above with respect to FIG. 1. More particularly, FIG. 4a shows the flexion-extension plane M1; FIG. 4b shows the abduction-adduction plane M2; and FIG. 4b shows the internal-external rotation plane M3.

Referring back to FIG. 3 and the embodiment where a GUI is displayed, a user can interact with the GUI to optionally select and enlarge a portion of the biomechanical profile for display. This option allows the user to visualize a particular degree of angular motion at a particular time during the movement; which is helpful in detecting relatively subtle knee joint motions.

Still with respect to the method 300, step 302 involves receiving as biomechanical data, at least one of kinematic, kinetic data and data reflective of ground reaction forces. The kinetic data and ground reaction force data are received from sensing devices such as force plates and treadmills equipped with sensing instruments.

In one embodiment, step 302 optionally involves receiving additional data such as patient information data, and clinical information data such as data entered into the system by a health practitioner (or retrieved from a database storing such patient and, or clinical data related to the patient). Patient data can comprise patient identification while clinical data can comprise previous diagnosis associated with the patient, or any other notes entered by a health care specialist for example. While other sources of data can be received in step 302, the method 300 and all other optional steps described herein, are achievable using as a sole input, kinematic data received from a set of motion sensors.

When step 302 involves receiving kinetic data, step 304 involves displaying the biomechanical profile with the kinetic data is optionally displayed within the profile. Similarly for ground reaction forces. In one embodiment, the displaying of the kinetic data or ground reaction forces involves generating a set of graphical illustrations according for example to three types of forces in play during the performance of the movement. In one embodiment, these forces respectively correspond to a vertical force, a lateral-medial force and a posterior-anterior force; as per the graphs illustrated in FIGS. 5a, 5b and 5c respectively. In the illustrated graphs of FIGS. 5a, 5b and 5c, the amount of ground reaction force is provided as a percentage of the patient's body weight (BW), while the time elapsed during the movement (here a gait cycle) is provided in terms of percentage of completion of the movement.

In addition to the above, the method 300 can also involve another step whereby the biomechanical profile is compared to a past biomechanical profile generated for the same knee joint. Based on such a comparison, an effect of a treatment is quantified in order to give an evaluation of a success or a failure of a given treatment. In the same way, a degradation/progression of a knee joint condition in time can be evaluated from a similar comparison. In one example, such a comparison involves superimposing past and current profiles (or pre and post treatment profiles).

Still in relation to FIG. 3, step 304 optionally involves normalizing the biomechanical data received in step 302 in order to generate normalized biomechanical profile for the knee joint. Alternatively, this option can be performed in or after step 310 prior to displaying the biomechanical profile in accordance with a given format, whereby the formatting involves the normalizing of the data.

Finally, it is noted that in one embodiment, the method 300 can also provide for the generating of a report. The report is built to include information such as patient data, the biomechanical profile (formatted as per a user's likings), and data pertaining to the identified problem as obtained from the performing of the method 300. In one instance, kinetic data, data on ground reaction forces, or a combination thereof, also is also provided in the report, optionally formatted as per a user's likings.

Other clinical data can also be part of the report, such as health practitioner notes and indications to the intention of the patient, or other practitioners.

The following provides examples of data which can be found in typical reports: a name of a conducting health professional; a date of consultation; a name of a patient; names of other individuals involved with either one of the consultation and report; a brief description of the context (e.g. an age of the patient; left, right knee joint pain; details on any injury; date and description of an incident if relevant; type and date of previous examinations when applicable; previous relevant knee joint injuries and/or pathologies when applicable); type of movement which was performed during the evaluation; descriptive summary of biomechanical deficits noted from the kinematic data and as reflected in the biomechanical profile (for example: a deficit in flexion movement during gait loading phase, limited knee joint flexion during push-off phase; important internal tibial rotation during loading phase); any other descriptive summary of biomechanical deficits noted via analysis of data on forces in play (i.e. kinetic or ground reaction forces, or combination thereof), such as loading phase time, forces involves with respect to one knee compared to the other knee (when data is available), deficits in breaking and pushing; other notes regarding video data (when provided in the profile)—i.e. for example any signs of limping; conclusions of post-examination; diagnosis(es) and recommendations of treatment(s).

It is noted that a computer-readable media having instructions for implementing a processor device to perform the above-described embodiments of the method 300 are also contemplated by the present disclosure.

Figure 4C:
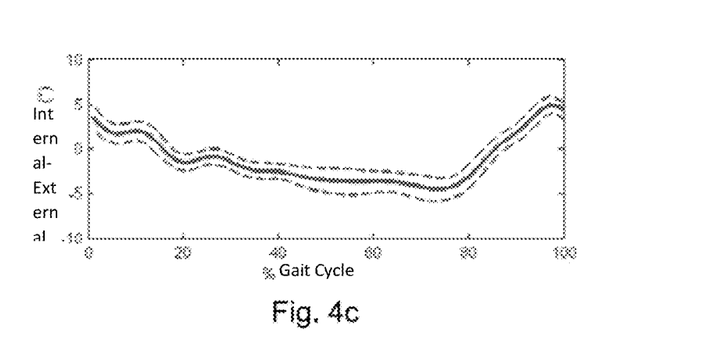
FIG. 4c is a graphical illustration of a degree of internal-external rotation of a knee joint during a gait cycle, in accordance with an embodiment.

Now referring to FIG. 4a, there is shown a graphical illustration of a degree of extension-flexion of one knee joint of a patient during a gait cycle, compared to a healthy range, in accordance with an embodiment. FIG. 4b is another graphical illustration of a degree of abduction-adduction of one knee joint of a patient during a gait cycle, in accordance with an embodiment; and FIG. 4c is yet another graphical illustration of a degree of internal-external rotation of one knee joint of a patient during a gait cycle, in accordance with an embodiment. In all three figures, it is noted that the gray range provides an indication of a healthy knee joint movement as seen in typical healthy subjects. The full line represents the mean angular motion for the patient's knee joint and the dashed lines represent the standard deviation with respect to the movement of a healthy knee joint.

The report is generated to include analytical comments regarding graphs such as those in FIGS. 4a, 4b and 4c. For example, from FIG. 4a it is possible to identify degrees of plane motions for each phase in the movement, from the initial contact of the foot with the ground (if the movement is gait), the loading phase, the stance phase, the push-off phase, to the swing phase). Total amplitude of the angular motion is also provided in terms of degrees, which is qualified as falling either in a healthy or unhealthy range.

Figure 5A:
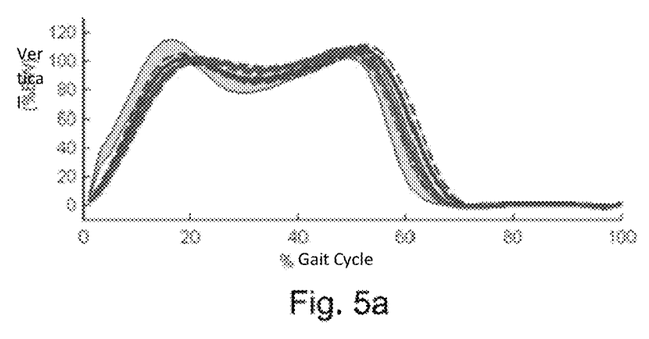
FIG. 5a is a graphical illustration of vertical ground reaction forces exerted during a gait cycle, in accordance with an embodiment.
Figure 5B:
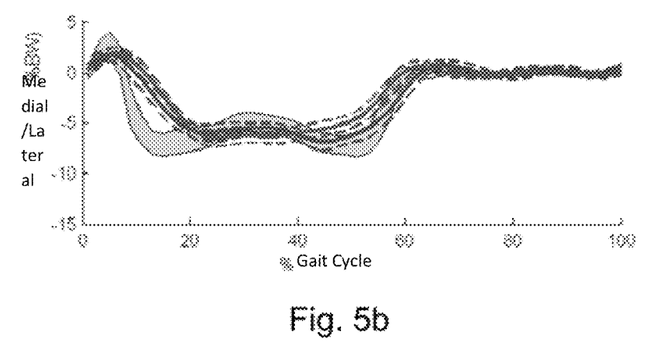
FIG. 5b is a graphical illustration of medial/lateral ground reaction forces exerted during a gait cycle, in accordance with an embodiment.
Figure 5C:
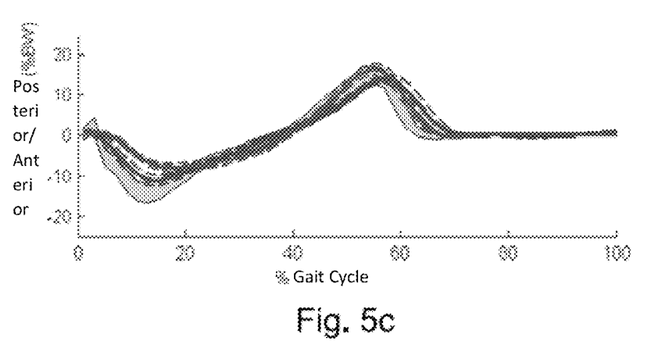
FIG. 5c is a graphical illustration of posterior/anterior ground reaction forces exerted during a gait cycle, in accordance with an embodiment.

Similar analytical comments are provided in the report regarding kinetic data (when applicable), as provided by graphical illustrations such as those of FIGS. 5a, 5b and 5c: FIG. 5a is a graphical illustration of vertical ground reaction forces exerted on a patient during a gait cycle, in accordance with an embodiment; FIG. 5b is a graphical illustration of medial/lateral ground reaction forces exerted on a patient during a gait cycle, in accordance with an embodiment; and FIG. 5c is a graphical illustration of posterior/anterior ground reaction forces exerted on a patient during a gait cycle, in accordance with an embodiment. All forces are indicated as a percentage of the patient's body weight (BW) while time is expressed as a percentage of completion of the gait cycle).

While preferred embodiments have been described above and illustrated in the accompanying drawings, it will be evident to those skilled in the art that modifications may be made therein without departing from the essence of this disclosure. Such modifications are considered as possible variants comprised in the scope of the disclosure.

The invention claimed is:

1. A method for identifying and characterizing a problem of a knee joint of a patient, the method comprising:
    receiving biomechanical data from sensors worn by the patient, the biomechanical data being representative of a movement of the knee joint during complete cycles of the movement of the knee joint;
    generating, in a processing device, a continuous biomechanical profile based on the biomechanical data, the continuous biomechanical profile comprising a continuous curve representative of the biomechanical data for the knee joint as a function of a percentage of the complete cycles of the movement of the knee joint, the continuous curve being a relation between a set of inputs and a set of outputs, where each input of the set of inputs represents a percentage of completion of the complete cycle of the movement of the knee joint and where each output of the set of outputs represents one of:
        a degree of extension-flexion of the knee joint of the patient corresponding to the percentage of completion of the complete cycle of the knee joint;
        a degree of abduction-adduction of the knee joint of the patient corresponding to the percentage of completion of the complete cycle of the knee joint;
        a degree of internal-external rotation of the knee joint of the patient corresponding to the percentage of completion of the complete cycle of the knee joint;
        a vertical ground reaction force exerted on the patient corresponding to the percentage of completion of the complete cycle of the knee joint;
        a medial/lateral ground reaction force exerted on the patient corresponding to the percentage of completion of the complete cycle of the knee joint; and
        a posterior/anterior ground reaction force exerted on the patient corresponding to the percentage of completion of the complete cycle of the knee joint;
    in the processing device, classifying the continuous biomechanical profile of the knee joint by considering all the outputs of the continuous curve representative of the biomechanical data in one of multiple classes of knee joint problems by applying a pattern recognition technique on the continuous biomechanical profile and a normative biomechanical profile associated to the one of the multiple classes, each one of the multiple classes corresponding to at least one knee joint problem comprising at least one of an injury, a pathology and a biomechanical deficit;
    based on the classifying, identifying, in the processing device, the problem as comprising the at least one knee joint problem of the one of the multiple classes; and
    archiving the problem identified in a storing device in communication with the processing device to make the problem accessible during consultation.

2. The method of claim 1, wherein the classifying comprises comparing the continuous biomechanical profile to a set of normative biomechanical profiles.

3. The method of claim 1, wherein the receiving comprises receiving the biomechanical data as the movement is being performed by the knee joint.

4. The method of claim 1, wherein the pattern recognition technique comprises at least one of: a parametric technique, a non parametric technique, a neural network, a nearest neighbour classification technique, a projection technique, a decision tree technique, a stochastic method, genetic algorithms with an unsupervised learning and clustering technique.

5. The method of claim 1, further comprising comparing the continuous biomechanical profile to a past continuous biomechanical profile generated for the same knee joint at an earlier time; and quantifying based on the comparing at least one of: a progression of the problem and an effect of a treatment performed on the knee joint.

6. The method of claim 1, wherein the biomechanical data are being collected from at least one of: a first plane of motion, a second plane of motion and a third plane of motion, wherein the receiving the biomechanical data comprises receiving at least one of kinematic data and kinetic data and wherein the first plane of motion, the second plane of motion and the third plane of motion are respectively representative of a plane of motion of the knee joint where a flexion-extension occurs, a plane of motion of the knee joint where an abduction-adduction occurs and a plane of motion of the knee joint where an internal-external rotation occurs.

7. The method of claim 1, wherein the identifying comprises identifying the problem as comprising at least two knee joint problems, the one of the multiple classes being associated to the at least two knee joint problems.

8. The method of claim 7, comprising sorting the at least two knee joint problems based on a respective degree of severity for each one of the at least two knee joint problems.

9. The method of claim 1, wherein the applying the pattern recognition technique on the continuous biomechanical profile and the normative biomechanical profile comprises determining an amount of similarity between the continuous biomechanical profile and the normative biomechanical profile.

10. The method of claim 9, comprising generating a report to include an identification of the problem; and displaying the report with the identification of the problem comprising at least one of: a name for the at least one knee joint problem; the amount of similarity; and the continuous biomechanical profile with an indication of a problematic area associated with the at least one knee joint problem.

11. The method of claim 1, comprising generating a recommendation based on a pre-established treatment associated to the at least one knee joint problem.

12. An apparatus for identifying and characterizing a problem of a knee joint of a patient, the apparatus comprising:

sensors for wearing by the patient, the sensors for gathering biomechanical data representative of a movement of the knee joint during complete cycles of the movement of the knee joint;
a processor in communication with the sensors; and
a memory device accessible by the processor, the memory device storing instructions for retrieval by the processor to implement the processor to:
receive the biomechanical data from the sensors;
generate a continuous biomechanical profile based on the biomechanical data, the continuous biomechanical profile comprising a continuous curve representative of the biomechanical data for the knee joint as a function of a percentage of the complete cycles of the movement of the knee joint, the continuous curve being a relation between a set of inputs and a set of outputs, where each input of the set of inputs represents a percentage of completion of the complete cycle of the movement of the knee joint and where each output of the set of outputs represents one of:
a degree of extension-flexion of the knee joint of the patient corresponding to the percentage of completion of the complete cycle of the knee joint;
a degree of abduction-adduction of the knee joint of the patient corresponding to the percentage of completion of the complete cycle of the knee joint;
a degree of internal-external rotation of the knee joint of the patient corresponding to the percentage of completion of the complete cycle of the knee joint;
a vertical ground reaction force exerted on the patient corresponding to the percentage of completion of the complete cycle of the knee joint;
a medial/lateral ground reaction force exerted on the patient corresponding to the percentage of completion of the complete cycle of the knee joint; and
a posterior/anterior ground reaction force exerted on the patient corresponding to the percentage of completion of the complete cycle of the knee joint;
classify the continuous biomechanical profile of the knee joint by considering all the outputs of the continuous curve representative of the biomechanical data in one of multiple classes of knee joint problems by applying a pattern recognition technique on the continuous biomechanical profile and a normative biomechanical profile associated to the one of the multiple classes, each one of the multiple classes corresponding to at least one knee joint problem comprising at least one of an injury, a pathology and a biomechanical deficit;
based on the classifying, identify the problem as comprising the at least one knee joint problem of the one of the multiple classes; and
archive the problem identified to allow retrieval of the problem during a medical consultation.

13. The apparatus of claim 12, further comprising a display device for displaying the problem identified.

14. The apparatus of claim 13, comprising a graphical user interface (GUI) for allowing a user interaction with the processor.

15. The apparatus of claim 12, wherein the sensors comprise a three-dimensional knee movement analyser having at least one of: an optical tracking device; an electromagnetic tracking device and an accelerometer based tracking device.

16. The apparatus of claim 12, wherein the instructions for applying the pattern recognition technique on the continuous biomechanical profile and the normative biomechanical profile comprise instructions for implementing the processor to compare the continuous biomechanical profile to the normative biomechanical profile.

17. The apparatus of claim 12, wherein the sensors comprise sensors for gathering at least one of kinematic data and kinetic data as biomechanical data.

18. The apparatus of claim 12, wherein the sensors comprise kinematic sensors for gathering kinematic data as a sole input.

19. A non-transitory computer readable media storing instructions for implementing a processor to identify a problem of a knee joint of a patient, the instructions comprising coding for implementing the processor to:
receive biomechanical data from sensors worn by the patient, the biomechanical data being representative of a movement of the knee joint during a-complete cycles of the movement of the knee joint;
generate a continuous biomechanical profile based on the biomechanical data, the continuous biomechanical profile comprising a continuous curve representative of the biomechanical data for the knee joint as a function of a percentage of the complete cycles of the movement of the knee joint, the continuous curve being a relation between a set of inputs and a set of outputs, where each input of the set of inputs represents a percentage of completion of the complete cycle of the movement of the knee joint and where each output of the set of outputs represents one of:
a degree of extension-flexion of the knee joint of the patient corresponding to the percentage of completion of the complete cycle of the knee joint;
a degree of abduction-adduction of the knee joint of the patient corresponding to the percentage of completion of the complete cycle of the knee joint;
a degree of internal-external rotation of the knee joint of the patient corresponding to the percentage of completion of the complete cycle of the knee joint;
a vertical ground reaction force exerted on the patient corresponding to the percentage of completion of the complete cycle of the knee joint;
a medial/lateral ground reaction force exerted on the patient corresponding to the percentage of completion of the complete cycle of the knee joint; and
a posterior/anterior ground reaction force exerted on the patient corresponding to the percentage of completion of the complete cycle of the knee joint;
classify the continuous biomechanical profile of the knee joint by considering all the outputs of the continuous curve representative of the biomechanical data in one of multiple classes of knee joint problems by applying a pattern recognition technique on the continuous biomechanical profile and a normative biomechanical profile associated to the one of the multiple classes, each one of the multiple classes corresponding to at least one knee joint problem comprising at least one of an injury, a pathology and a biomechanical deficit;
based on the classifying, identify the problem as comprising the at least one knee joint problem of the one of the multiple classes; and
archive the problem identified in a storing device in communication with the processing device to make the problem accessible during consultation.

* * * * *

UNITED STATES PATENT AND TRADEMARK OFFICE
CERTIFICATE OF CORRECTION

PATENT NO. : 9,532,732 B2  
APPLICATION NO. : 12/772701  
DATED : January 3, 2017  
INVENTOR(S) : Mezghani et al.

Page 1 of 1

It is certified that error appears in the above-identified patent and that said Letters Patent is hereby corrected as shown below:

On the Title Page

Item (75), add --Michelle Laflamme--

Signed and Sealed this  
Twelfth Day of February, 2019

Andrei Iancu  
*Director of the United States Patent and Trademark Office*